United States Patent
Gross et al.

(10) Patent No.: US 8,648,055 B2
(45) Date of Patent: Feb. 11, 2014

(54) VIRUCIDAL PROPERTIES OF VARIOUS FORMS OF SOPHOROLIPIDS

(75) Inventors: Richard A Gross, Plainview, NY (US); Vishal Shah, Oakdale, NY (US); Gustavo Doncel, Norfolk, VA (US)

(73) Assignee: SyntheZyme, LLC, Brooklyn, NY (US)

( * ) Notice: Subject to any disclaimer, the term of this patent is extended or adjusted under 35 U.S.C. 154(b) by 170 days.

(21) Appl. No.: 13/412,100

(22) Filed: Mar. 5, 2012

(65) Prior Publication Data

US 2012/0231068 A1 Sep. 13, 2012

Related U.S. Application Data

(62) Division of application No. 13/112,122, filed on May 20, 2011, which is a division of application No. 10/804,778, filed on Mar. 19, 2004, now abandoned.

(60) Provisional application No. 60/456,208, filed on Mar. 20, 2003.

(51) Int. Cl.
  *A01N 43/04* (2006.01)
  *A61K 31/715* (2006.01)
  *A61K 31/70* (2006.01)

(52) U.S. Cl.
  USPC .............................. 514/53; 514/25

(58) Field of Classification Search
  CPC .................................. A61K 31/7028
  USPC ...................................... 514/25, 53
  See application file for complete search history.

(56) References Cited

FOREIGN PATENT DOCUMENTS

WO   WO 2004/044216 A1 *   5/2004   ............. C12P 19/44

\* cited by examiner

*Primary Examiner* — Scarlett Goon
(74) *Attorney, Agent, or Firm* — Laurence P. Colton; Smith Risley Tempel Santos LLC

(57) ABSTRACT

A method for neutralizing or inactivating a virus, and neutralizing or inactivating HIV using sophorolipids having antiviral properties produced by synthesizing the sophorolipid by fermentation of *Candida bombicola* in a fermentation media to form a natural mixture of lactonic sophorolipids compounds and non-lactonic sophorolipids compounds and utilizing the natural mixture as an antiviral agent, and/or separating the lactonic sophorolipids from the natural mixture to form a lactonic fraction and mixing all remaining fractions to form a non-lactonic fraction and utilizing the lactonic fraction and/or the non-lactonic fraction as an antiviral agent, and sophorolipid compounds for use as antiviral agents.

3 Claims, 1 Drawing Sheet

Structures of sophorolipids produced by *Candida bombicola*.
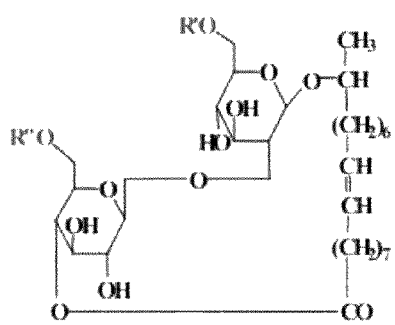
1. R' = R'' = Ac or H
2. R' = Ac; R'' = H
3. R' = H; R'' = Ac
4. R' = R'' = H
a. Lactonic sophorolipid
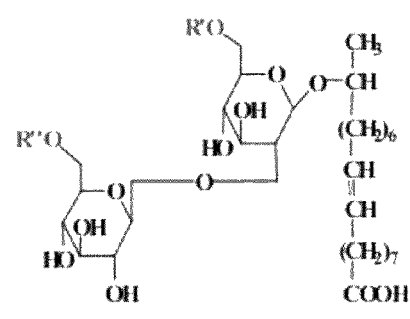
5. R' = R'' = Ac or H
6. R' = Ac; R'' = H
7. R' = H; R'' = Ac
8. R' = R'' = H
b. Open ring sophorolipid

VIRUCIDAL PROPERTIES OF VARIOUS FORMS OF SOPHOROLIPIDS

STATEMENT OF RELATED APPLICATIONS

This application is a divisional and claims the benefit of U.S. patent application Ser. No. 13/112,122 having a filing date of 20 May 2011, which is a divisional and claims the benefit of U.S. patent application Ser. No. 10/804,778 having a filing date of 19 Mar. 2004, which is a nonprovisional patent application that is based on and claims the benefit of U.S. Provisional Patent Application No. 60/456,208 having a filing date of 20 Mar. 2003.

BACKGROUND OF THE INVENTION

1. Technical Field

The present invention relates generally to the field of uses for sophorolipids and more specifically to the field of uses of sophorolipids as antiviral agents.

2. Prior Art

First described in 1961, sophorolipids occur as a mixture of macrolactone and free acid structures that are acetylated to various extents at the primary hydroxyl position of the sophorose ring. Gorin, P. A. et al., Can. J. Chem., vol. 39, p. 846 (1961). Careful examinations have revealed that at least eight structurally different sophorolipids are produced. Davila, A. M. et al., J. Chromatogr., vol. 648, p. 139 (1993). The main component of sophorolipids is 17-hydroxyoctadecanoic acid and its corresponding lactone. Tulloch, A. P. et al., Can. J. Chem., vol. 40, p. 1326 (1962) and Tulloch, A. P. et al., Can J. Chem., vol. 46, p. 3337 (1968).

Work has been carried out to tailor sophorolipid structure during in vivo formation, mainly by the selective feeding of different lipophilic substrates. Zhou, Q. -H., et al., J. Am. Oil Chem. Soc., vol. 72, p. 67 (1995). Also unsaturated C-18 fatty acids of oleic acid may be transferred unchanged into sophorolipids. Rau, U. et al., Biotechnol. Lett., vol. 18, p. 149 (1996). However, while physiological variables during fermentation have provided routes to the variation of sophorolipid composition, this has not led to well-defined pure compounds.

Existing data suggests that glycolipids may be useful in treating very severe immune disorders. For example, glycolipids have been reported to be of interest for in vivo cancer treatment/antitumor cell activity, treatment of autoimmune disorders, in vivo and in vitro antiendotoxic (septic) shock activity, regulation of angiogenesis, and apoptosis induction, all by cytokine activity. See, e.g., U.S. Pat. No. 5,597,573 to Massey, U.S. Pat. No. 5,514,661 to Piljac, U.S. Pat. No. 5,648,343 to Carlson, and the references cited in notes 9-13 of Bisht, K. S. et al., J. Org. Chem., vol. 64, pp. 780-789 (1999).

At the turn of the millennium, the Joint United Nations Programme on HIV/AIDS (UNAIDS) and the World Health Organization (WHO) estimated that 34.3 million adults and children were living with HIV/AIDS. More than 18 million had already died of the disease. An estimated 95% of all people living with HIV/AIDS live in developing countries where limited resources and cultural factors make containment of the epidemic especially difficult.

Most HIV infections are transmitted through heterosexual intercourse, and in many areas women are disproportionately affected. About 55% of adults living with HIV/AIDS in sub-Saharan Africa, for example, are women.

The impact of the current level of HIV seroprevalence is enormous in terms of mortality, resource depletion, and human suffering. There is clearly an unmet need for treatment of those already infected. However, there is also a desperate need to prevent further infection.

Efforts to prevent HIV transmission have centered around three approaches: behavioral change (safer sex), the development of a vaccine, and development of a microbicide. In the context of prevention of sexually transmitted diseases (STDs), microbicides are compounds that, when applied topically, protect the body's mucosal surfaces from infection by STD-causing pathogens.

The world's population is increasing at a sustained rate. But population growth is disproportionately high in developing countries with limited resources, those that are especially exposed to infectious diseases such as AIDS. Fertility control and prevention of sexually transmitted diseases are high-priority issues in the public health agenda of developing nations.

Thus, there exists an urgent need to develop new and improved methods for fertility control and prevention of unwanted pregnancies and sexually transmitted infections. It is to the development of sophorolipids for pharmaceutical and industrial purposes, and in particular as microbicides and spermicides or vaginal contraceptives, that the present invention is directed.

BRIEF SUMMARY OF THE INVENTION

Sophorolipids are microbial extracellular glycolipids produced by resting cells of Candida bombicola. The chemical composition of sophorolipid is constituted by a disaccharide sugar viz. sophorose and a fatty acid or an ester group. Candida bombicola produces the sophorolipids as a mixture of macrolactones and free acid structures that are acetylated to various extents at the primary hydroxyl sophorose ring positions (FIG. 1). Bisht, K. S. et al., J. Org. Chem., vol. 64, pp. 780-789 (1999).

For this invention, a natural mixture of sophorolipids was synthesized by fermentation of Candida bombicola. Lactonic sophorolipid was separated from the crude mixture. A lactonic fraction was collected separately and all other fractions were mixed to form a non-lactonic sophorolipid mixture. Ethyl 17-L-[(2'-O-β-D-glucopyranosyl-β-D-glucopyranosyl)-oxy]-cis-9-octadecenoate then was synthesized and then further treated to obtain Ethyl 17-L[(2'-O-β-D glucopyranosyl-β-D-glucopyranosyl)-oxy]-cis-9-octadecenoate 6',6"-diacetate. Hexyl 17-L-[(2'-O-β-D-glucopyranosyl-β-D-glucopyranosyl)-oxy]-cis-9-octadecenoate also was synthesized.

A quantity of sperm was treated with sophorolipids and the ability of the sophorolipids to immobilize and kill the sperm was measured. All forms of sophorolipids were highly effective as spermicidal agents. Also, sophorolipids were evaluated as virucidal agents using the human immunodeficiency virus (HIV) as model organism. All the sophorolipids tested showed virucidal activity. The ethyl ester form of sophorolipid was highly effective as an antiviral agent. Howsoever, other forms of sophorolipids were also effective.

Thus, the present invention relates to the application of sophorolipids in the field of medicine to prevent and treat viral infections. Additionally, the present invention relates to the application of sophorolipids in the field of medicine as contraceptive agents. Further, while sophorolipids can find applications in diverse fields, the present invention relates to sophorolipids as antiviral and spermicidal contraceptive agents.

These features, and other features and advantages of the present invention, will become more apparent to those of ordinary skill in the relevant art when the following detailed description of the preferred embodiments is read in conjunction with the appended drawing and tables.

BRIEF DESCRIPTION OF THE FIGURE

FIG. 1 contains representative structures of sophorolipids produced by *Candida bombicola*, with FIG. 1a showing a lactonic sophorolipid and FIG. 1b showing an open-ring sophorolipid.

DETAILED DESCRIPTION OF THE PREFERRED EMBODIMENTS

1. Sophorolipid Fermentation

Sophorolipids were synthesized by fermentation of *Candida bombicola*. The fermentation media was composed of glucose 100 g, yeast extract 10 g, urea 1 g and oleic acid 40 g in 1000 ml of water. After 7 days of fermentation, sophorolipid was extracted thrice using ethyl acetate. The extracts were pooled and the solvent then was removed. The obtained product was then washed with hexane to remove the residual fatty acids. This was "natural" sophorolipid. The sophorolipid was dried in a vacuum desiccator.

2. Preparation of Lactonic Sophorolipid

Column chromatographic separations were performed over silica gel 70 (Aldrich Chemical Co.) to separate lactonic sophorolipid from the crude mixture. 50 g of silica gel was used to pack a glass column (5 cm×50 cm) in the eluent ($CHCl_3$/MeOH mixture). 200 ml of eluent was run through the column before the natural mixture (dissolved in a minimal volume of eluent) was loaded onto the top of the column matrix. Different fractions were subsequently eluted (1 mL/min). A lactonic fraction was collected separately and all other fractions were mixed to form non-lactonic sophorolipid mixture.

3. Synthesis of Ethyl 17-L[(2'-O-β-D glucopyranosyl-β-D-glucopyranosyl)-oxy]-cis-9-octadecenoate 6',6"-diacetate Ethyl 17-L-[(2'-O-β-D-glucopyranosyl-β-D-glucopyranosyl)-oxy]-cis-9-octadecenoate was synthesized by adding 2 g of dry crude sophorolipid and 2.5 mL 0.021 N sodium ethoxide in methanol solution to a 100 mL round-bottomed flask equipped with a reflux condenser. The reaction assembly was protected from atmospheric moisture by a $CaCl_2$ guard tube. The reaction mixture was refluxed for 3 hr, cooled to room temperature (30° C.), and acidified using glacial acetic acid. The reaction mixture was concentrated by rotoevaporation and poured with stirring into 100 mL of ice-cold water that resulted in the precipitation of the sophorolipid ethylester as a white solid. The precipitate was filtered, washed with ice-water, and lyophilized.

The synthesized Ethyl 17-L-[(2'-O-β-D-glucopyranosyl-β-D-glucopyranosyl)-oxy]-cis-9-octadecenoate (500 mg) was dissolved in 20 mL of dry tetrahydrofuran (THF). To this solution were added vinyl acetate (2 mL) and Novozym 435 (1 g), and the suspension was stirred magnetically at 35° C. for 96 hr. The enzyme was filtered off, the solvent was evaporated, and the product was purified by column chromatography (eluent $CHCl_3$/MeOH, 9:1) to give 490 mg of Ethyl 17-L[(2'-O-β-D glucopyranosyl-β-D-glucopyranosyl)-oxy]-cis-9-octadecenoate 6',6"-diacetate.

The synthesis of other related compounds, such as methyl- and butyl-based compounds, can be accomplished by substituting sodium methoxide or sodium butoxide respectively for the sodium ethoxide, resulting in sophorolipid methylester and sophorolipid butylester, respectively. The amount of dry natural sophorolipid and the amount and normality of the sodium $(CH_2)_n$oxide can be varied appropriately by those of ordinary skill in the art without undue experimentation. Other types of suitable sophorolipids also can be synthesized by those of ordinary skill in the art without undue experimentation.

4. Synthesis of Hexyl 17-L[(2'-O-β-D glucopyranosyl-β-D-glucopyranosyl)-oxy]-cis-9-octadecenoate Hexyl 17-L-[(2'-O-β-D-glucopyranosyl-β-D-glucopyranosyl)-oxy]-cis-9-octadecenoate was synthesized by adding 2 g of dry natural sophorolipid and 2.5 mL 0.021 N sodium hexanoxide in hexanol solution to a 100 mL round-bottomed flask equipped with a reflux condenser. The reaction assembly was protected from atmospheric moisture by a $CaCl_2$ guard tube. The reaction mixture was refluxed for 3 hr, cooled to room temperature (30° C.), and acidified using glacial acetic acid. The reaction mixture was concentrated by rotoevaporation and poured with stirring into 100 mL of ice-cold water that resulted in the precipitation of the sophorolipid ethylester as a white solid. The precipitate was filtered, washed with ice-water, and lyophilized.

5. Spermicidal Study

Motility and viability time-responses were studied with a sophorolipid testing concentration of 0.3 mg/mL. At this concentration no effect of the solvent was observed. All sperm used for this experiment and throughout the study were obtained from human semen samples through a one hour swim-up separation technique in BWW medium+0.1% HSA.

100 uL of swim-up sperm were incubated with 1 uL of compound for the time points of 2 min, 30 min, 2 hrs, and 4 hrs and assessed for progressive motility ("real-time" assessment). n=5 for all time points. Co-incubation samples were diluted with 1 mL of BWW medium+0.1% HSA. The tubes were centrifuged, the supernatant removed, and the sperm resuspended in the original volume of 100 uL BWW+0.1% HSA and incubated at 37° C., 5% $CO_2$. At 30 min post-washing, motility was again assessed. After the 30 min post-wash assessment, 900 uL of HOS medium was added to the sample and tubes were incubated for 30 min at 37° C. Post-incubation, samples were assessed for viability. Motility and viability were quantified "manually" under dark field microscopy (Nikon E-800).

6. Viral Inactivation Study Using Cell-Free HIV

Pre-titered concentrated virus (HIV-1 RF) stock (10 μL) was mixed with 90 μL of the test agent formulation in microtubes. At the end of the two-minute exposure period, serial 10-fold dilutions were carried out with a multichannel pipettor so that the sample dilutions were performed simultaneously. Aliquots (100 μL) of the serial dilutions were then transferred simultaneously to another 96-well plate which had been pre-seeded with MT-2 cells in RPMI medium supplemented with FBS. Four wells were used for each dilution of virus. The cultures were incubated at 37° C. in a humidified atmosphere of 5% $CO_2$. The cultures were scored microscopically for virus-induced cytopathic effect and agent-induced cytotoxicity on day 4 and 7 of incubation, and day 7 reported. Cultures were routinely maintained 2 to 3 days after initial analysis, and observed visually and microscopically for abnormalities.

7. Results and Discussion

As shown in Table 1, all four sophorolipid compounds tested immobilized almost 100% of spermatozoa in the shortest time studied (2 min.). This effect was irreversible since motility did not recover after washing off the compounds and further incubating the sperm for 30 min. in fresh medium. Such immotility may be due to a severe alteration of the membrane selective permeability, since the sperm viability test revealed that almost 100% of spermatozoa had their membrane integrity compromised.

As shown in Table 2, all four sophorolipid compounds tested displayed some degree of virucidal activity. Our criterion to consider a result as "positive" indicates a minimum reduction in virus titer of 2 logs. The best selectivity index was displayed by Ethyl 17-L-[(2'-O-β-D-glucopyranosyl-β-D-glucopyranosyl)-oxy]-cis-9-octadecenoate, which showed high activity and reduced cytotoxicity.

Thus, the invention claims the use of natural mixture, lactonic, 6',6"-diacetate, Ethyl ester, Hexyl ester sophorolipids as spermicidal and virucidal agents. The applications in field of medicine, particularly in the areas of contraception and infectious diseases, would be tremendous, providing new means for "safe sex" as well as to treat and prevent viral infections, apart from other applications.

8. Utilizing the Natural Mixture, the Lactonic Fraction, and/or the Non-Lactonic Fraction of Sophorolipids as a Spermicidal and/or Antiviral Agent The present invention also is a method for producing sophorolipids having spermicidal and/or antiviral properties and using either the natural mixture, the lactonic fraction of the mixture, the non-lactonic fraction of the mixture, and/or combinations of these as antiviral agents or spermicidal agents.

One such method for producing sophorolipids having spermicidal and/or antiviral properties comprises the steps of (a) synthesizing the sophorolipid by fermentation of Candida bombicola in a fermentation media to form a natural mixture of lactonic sophorolipids and non-lactonic sophorolipids; (b) utilizing the natural mixture as a spermicidal and/or antiviral agent; (c) separating the lactonic sophorolipids from the natural mixture to form a lactonic fraction and mixing all remaining fractions to form a non-lactonic fraction; (d) utilizing the lactonic fraction as an spermicidal and/or antiviral agent; and (e) utilizing the non-lactonic fraction as a spermicidal and/or antiviral agent.

Another such method for producing sophorolipids having spermicidal and/or antiviral properties comprises the steps of: (a) synthesizing the sophorolipid by fermentation of Candida bombicola in a fermentation media to form a natural mixture of lactonic sophorolipids and non-lactonic sophorolipids; and (b) utilizing the natural mixture as a spermicidal and/or antiviral agent.

Another such method for producing sophorolipids having spermicidal and/or antiviral properties comprises the steps of: (a) synthesizing the sophorolipid by fermentation of Candida bombicola in a fermentation media to form a natural mixture of lactonic sophorolipids and non-lactonic sophorolipids; (b) separating the lactonic sophorolipids from the natural mixture to form a lactonic fraction and mixing all remaining fractions to form a non-lactonic fraction; and (c) utilizing the lactonic fraction as an spermicidal and/or antiviral agent.

Another such method for producing sophorolipids having spermicidal and/or antiviral properties comprises the steps of: (a) synthesizing the sophorolipid by fermentation of Candida bombicola in a fermentation media to form a natural mixture of lactonic sophorolipids and non-lactonic sophorolipids; (b) separating the lactonic sophorolipids from the natural mixture to form a lactonic fraction and mixing all remaining fractions to form a non-lactonic fraction; and (c) utilizing the non-lactonic fraction as an spermicidal and/or antiviral agent.

Preferably, these methods use a 17-L-[(2'-O-β-D-glucopyranosyl-β-D-glucopyranosyl)-oxy]-cis-9-octadecenoate based sophorolipid. Even more preferably, the 17-L-[(2'-O-β-D-glucopyranosyl-β-D-glucopyranosyl)-oxy]-cis-9-octadecenoate based sophorolipid is selected from the group consisting of 17-L-[(2'-O-β-D-glucopyranosyl-β-D-glucopyranosyl)-oxy]-cis-9-octadecenoate-6',6"-diacetate, Hexyl 17-L[(2'-O-β-D glucopyranosyl-β-D-glucopyranosyl)-oxy]-cis-9-octadecenoate, and Ethyl 17-L[(2'-O-β-D glucopyranosyl-β-D-glucopyranosyl)-oxy]-cis-9-octadecenoate.

9. Delivery Mechanisms

The sophorolipid compounds disclosed herein can be delivered in many different forms. Illustrative examples of the delivery forms include a gel, a film, a foam, a suppository, a pessary, a liposomic formulation, as a liquid imbibed in a sponge, and as a liquid being released from an intravaginal or intrauterine delivery system. Those of ordinary skill in the art can chose other delivery systems and formulate the novel sophorolipid into the delivery system chosen without undue experimentation.

10. Combination Systems

The novel sophorolipids disclosed herein also can be combined in various forms and with other antiviral agents or spermicidal agents to result in alternative novel antiviral and spermicidal agents. For example, one such method of combining the novel sophorolipids is to produce a sophorolipid synthesized by fermentation of Candida bombicola in a fermentation media to form a natural mixture of lactonic sophorolipids and non-lactonic sophorolipids and to combine this with at least one sophorolipid selected from the group consisting of 17-L-[(2'-O-β-D-glucopyranosyl-β-D-glucopyranosyl)-oxy]-cis-9-octadecenoate-6',6"-diacetate, Ethyl 17-L-[(2'-O-β-D-glucopyranosyl-β-D-glucopyranosyl)-oxy]-cis-9-octadecenoate, Hexyl 17-L-[(2'-O-β-D-glucopyranosyl-β-D-glucopyranosyl)-oxy]-cis-9-octadecenoate, and combinations thereof. These combinations can be used as antiviral agents and as spermicidal agents.

Further, the novel sophorolipids disclosed herein can be made and/or used in combination with one or more known antiviral agents or one or more known spermicidal agents to produce alternative antiviral agents and spermicidal agents. Those of ordinary skill in the art can choose the appropriate or desired known antiviral agents or spermicidal agents to combine with the novel sophorolipds to result in an alternate antiviral agent or spermicidal agent, respectively, without undue experimentation.

The foregoing detailed description of the preferred embodiments and the appended FIGURE and tables have been presented only for illustrative and descriptive purposes. They are not intended to be exhaustive nor to limit the scope and spirit of the invention. The embodiments were selected and described to best explain the principles of the invention and its practical applications. One skilled in the art will recognize that many variations can be made to the invention disclosed in this specification without departing from the scope and spirit of the invention. For instance, sophorolipids have been tested against HIV but will most likely be active against other retrovirus, herpes virus, papillomavirus, and other viruses as well.

TABLE 1

Motility and Viability Time Response

| Compound | Initial Solvent | Time | Conc (mg/mL) | Real-Time Motility (%) | Post-Dilution Motility (%) | Post-Dilution Viability (%) | n |
|---|---|---|---|---|---|---|---|
| SL-1 | DMSO | 2 min | 0.3 | 3.26 ± 3.36 | 3.10 ± 6.66 | 3.07 ± 6.86 | 5 |
| | | 30 min | 0.3 | 0.00 ± 0.00 | 0.00 ± 0.00 | 0.50 ± 1.11 | 5 |
| | | 2 hour | 0.3 | 0.00 ± 0.00 | 0.00 ± 0.00 | 0.00 ± 0.00 | 5 |
| SLET | DMSO | 2 min | 0.3 | 0.73 ± 0.81 | 3.37 ± 3.87 | 2.36 ± 5.29 | 5 |
| | | 30 min | 0.3 | 0.00 ± 0.00 | 0.00 ± 0.00 | 1.00 ± 2.24 | 5 |
| | | 2 hour | 0.3 | 0.00 ± 0.00 | 0.00 ± 0.00 | 0.00 ± 0.00 | 5 |
| SLHEX | DMSO | 2 min | 0.3 | 1.26 ± 1.22 | 1.55 ± 2.18 | 2.27 ± 3.22 | 5 |
| | | 30 min | 0.3 | 0.00 ± 0.00 | 0.00 ± 0.00 | 1.10 ± 2.46 | 5 |
| | | 2 hour | 0.3 | 0.00 ± 0.00 | 0.00 ± 0.00 | 0.00 ± 0.00 | 5 |
| SLETDA | DMSO | 2 min | 0.3 | 0.00 ± 0.00 | 0.00 ± 0.00 | 0.40 ± 0.90 | 5 |
| | | 30 min | 0.3 | 0.00 ± 0.00 | 0.00 ± 0.00 | 0.20 ± 0.45 | 5 |
| | | 2 hour | 0.3 | 0.00 ± 0.00 | 0.00 ± 0.00 | 0.00 ± 0.00 | 5 |
| DMSO 1:100 | — | 2 min | 0.3 | 99.57 ± 1.22 | 99.27 ± 1.12 | 99.49 ± 0.78 | 5 |
| | | 30 min | 0.3 | 99.28 ± 0.85 | 99.66 ± 0.50 | 99.40 ± 0.80 | 5 |
| | | 2 hour | 0.3 | 99.19 ± 1.27 | 99.27 ± 1.18 | 99.20 ± 0.73 | 5 |

*Values expressed as Mean ± Standard Deviation

TABLE 2

Cell-Free Inactivation Assay

| Drug | Initial Solvent | Percent of Agent During Exposure | TCTD50 Cytotoxicity | Log Reduction in Virus Titer |
|---|---|---|---|---|
| SL-1 | DMSO | 0.3 | 1.5 | 1.7 |
| | | 0.09 | 1.5 | 1.7 |
| | | 0.03 | ≤0.5 | 1.7 |
| SLET | DMSO | 0.3 | 1.5 | 4.3 |
| | | 0.09 | ≤0.5 | 3.3 |
| | | 0.03 | ≤0.5 | 2.0 |
| SLETDA | DMSO | 0.3 | 1.5 | ≥4.5 |
| | | 0.09 | 1.5 | ≥4.5 |
| | | 0.03 | ≤0.5 | 1.7 |
| SLHEX | DMSO | 0.3 | 1.5 | 4.0 |
| | | 0.09 | ≤0.5 | 3.0 |
| | | 0.03 | ≤0.5 | 0 |
| DMSO | | 1:10 dil | ≤0.5 | 0 |
| | | 1:32 dil | ≤0.5 | 0 |
| | | 1:100 dil | ≤0.5 | 0 |
| | | 1:320 dil | ≤0.5 | 0 |
| Virus Control = 6.0 – log10 | | TCID50/0.1 mL | | |

$TCID_{50}$: The minimum drug concentration that inhibits HIV-induced cytopathic effect by 50%, calculated by using a regression analysis program for semilog curve fitting.
$TCTD_{50}$: The minimum drug concentration that reduces cell viability by 50%

What is claimed is:

1. A method for neutralizing or inactivating HIV by treating the HIV with an effective amount of a 17-L-[(2'-O-β-D-glucopyranosyl-β-D-glucopyranosyl)-oxy]-cis-9-octadecenoate sophorolipid compound selected from the group consisting of:
 ethyl 17-L-[(2'-O-β-D-glucopyranosyl-β-D-glucopyranosyl)-oxy]-cis-9-octadecenoate-6',6"-diacetate;
 hexyl 17-L[(2'-O-β-D glucopyranosyl-β-D-glucopyranosyl)-oxy]-cis-9-octadecenoate;
 ethyl 17-L[(2'-O-β-D glucopyranosyl-β-D-glucopyranosyl)-oxy]-cis-9-octadecenoate; and
 combinations thereof.

2. The method as claimed in claim 1, wherein the sophorolipid compound is in a form selected from the group consisting of a gel, a film, a foam, a suppository, a pessary, a liposomic formulation, a liquid imbibed in a sponge, and a liquid being released from an intravaginal or intrauterine delivery system.

3. The method as claimed in claim 1, further comprising combining the 17-L-[(2'-O-β-D-glucopyranosyl-β-D-glucopyranosyl)-oxy]-cis-9-octadecenoate sophorolipid compound with an antiviral agent.

* * * * *